United States Patent [19]
Golding et al.

[11] Patent Number: 5,890,883
[45] Date of Patent: Apr. 6, 1999

[54] ROTODYNAMIC PUMP WITH NON-CIRCULAR HYDRODYNAMIC BEARING JOURNAL

[75] Inventors: Leonard A. R. Golding, Moreland Hills; William A. Smith, Lyndhurst, both of Ohio

[73] Assignee: The Cleveland Clinic Foundation, Cleveland, Ohio

[21] Appl. No.: 820,756

[22] Filed: Mar. 19, 1997

[51] Int. Cl.$^6$ .................................................. F04B 35/04
[52] U.S. Cl. .................................. 417/423.12; 604/151
[58] Field of Search ........................... 417/423.7, 423.1, 417/423.12, 423.13, 423.14; 604/151

[56] References Cited

U.S. PATENT DOCUMENTS

| | | |
|---|---|---|
| 5,017,103 | 5/1991 | Dahl . |
| 5,049,134 | 9/1991 | Golding et al. . |
| 5,098,256 | 3/1992 | Smith . |
| 5,100,374 | 3/1992 | Kageyama . |
| 5,118,264 | 6/1992 | Smith . |
| 5,145,333 | 9/1992 | Smith . |
| 5,242,268 | 9/1993 | Fukazawa et al. . |
| 5,324,177 | 6/1994 | Golding et al. .................. 417/423.7 |
| 5,348,444 | 9/1994 | Metzinger et al. . |
| 5,370,509 | 12/1994 | Golding et al. .................. 417/423.7 |
| 5,399,074 | 3/1995 | Nose et al. . |
| 5,695,471 | 12/1997 | Wampler .......................... 417/423.7 |
| 5,713,730 | 2/1998 | Nose et al. ...................... 417/423.12 |

OTHER PUBLICATIONS

Leonard A. R. Golding, et al. "The Cleveland Clinic Rotodynamic Pump Program" *Artificial Orgnas* 20(6):481–484, Blackwell Science, Inc., Boston Jan. 1996.

*Primary Examiner*—Charles G. Freay
*Attorney, Agent, or Firm*—Fay, Sharpe, Beall, Fagan, Minnich & McKee

[57] ABSTRACT

A blood pump incorporates a blood lubricated journal bearing that is characterized by a non-circular geometry. In one embodiment, the stationary bearing element, or stator, of the bearing is provided with a semi-elliptical shaped outer surface in an area opposite the load bearing film. The journal bearing configuration ensures that the blood flow therethrough is adequate, that the integrity of the blood is preserved and that bearing stability is maintained.

22 Claims, 4 Drawing Sheets

ROTODYNAMIC PUMP WITH NON-CIRCULAR HYDRODYNAMIC BEARING JOURNAL

BACKGROUND OF THE INVENTION

The present invention relates to the art of pumps and, more particularly, to pumps suitable for use as heart or blood pumps or as ventricular assist devices. The invention is particularly applicable to pumps for the blood of a living person, or animal, intended to assume entirely or assist the pumping function of the biologic heart. It will be recognized, however, that the invention has wider application because it may generally be applied to environments that generally involve bearings, including hydrodynamic journal bearings.

There has been significant effort in the field of biomedical engineering to provide artificial blood pumps, i.e., non-biological devices that assist or assume entirely the pumping functions of the human heart. These devices are surgically introduced within the human cardiovascular system. Because of the unique biological environment in which they operate, blood pumps must satisfy very exacting operational requirements that relate primarily to the prevention of blood damage and the prevention of the loss of blood from the circulatory system. Of course, the dependability and longevity of operation of the device is also a major concern.

Blood pumps impart fluid motion to the blood that is not ordinarily experienced during normal biological processes. This fluid motion may jeopardize the integrity of the blood cells and present an excessive risk that hemolysis—the damage of blood cell membranes—will occur because of the excessive fluid shear and frictional forces experienced by the pumped blood. This risk is especially significant in small blood passages within the pump, typically including the fluid flow path between the pump impeller and housing. Blood cell integrity in the pumped blood is also at risk because of the heat generated by friction between the moving parts of the blood pump. Frictional energy may result ultimately in thrombosis—the undesirable clotting or coagulation of blood. It may also increase the potential for the formation of protein deposits within the pump structure or within the blood. To counter these effects, blood flow within the pump is often relied upon to provide a washing and cooling effect to the blood pump parts. In addition, blood has been used to lubricate the moving parts of the pump.

A blood pump that exemplifies the state of the art is disclosed in U.S. Pat. No. 5,342,177 to Golding et al, the subject matter of which is incorporated herein by reference. The invention disclosed therein provides a rotodynamic blood pump that utilizes a blood lubricated journal bearing between an annular rotor element, which includes an impeller for imparting axial motion to the blood, and a stationary bearing element, or stator, disposed inside the rotor. A driving means is disposed within the stator and is magnetically coupled to the rotor. The annular rotor cooperates with the axial extension to define two fluid passages. A primary fluid passage leads from the pump inlet to the outlet. A secondary passage provides a continuous flow thru otherwise stagnant areas of the pump. At least a portion of this second passage is narrowed to form a radial fluid bearing between the rotor and stator. In accordance with one aspect of the invention disclosed in U.S. Pat. No. 5,324,177, the axis of the drive element housed within the stator is deliberately offset from the rotor axis. In this way, a known magnetic force is provided to bias the rotor in opposition to the bearing fluid pressure forces and increased bearing stability is achieved. The use of blood flow for washing, cooling and, especially, the lubricating functions in journal bearings of state of the art blood pumps brings with it unique problems relating to blood integrity preservation.

Generally speaking, journal bearings are often used to support a rotating cylindrical member that is subject to a radial load. These bearings rely on a load-carrying film or cushion of lubricating fluid that resides between the rotating and stationary member on a side that is opposite the radial load. The operating principle behind a fluid film bearing is that the lubricating fluid is entrained by the journal into the load bearing film by the fluid viscosity. If the fluid passage is convergent in the direction of rotation of the bearing rotor, this action results in a pressure field in the load bearing film which provides sufficient force to float the journal and carry the radial load. As the passage converges, fluid pressure will increase. Conversely, if the passage diverges, fluid pressure will decrease and cavitation therefore becomes a concern in fluid bearing design. As a general rule, fluid bearing operation is characterized primarily by the viscosity of the lubricant, the speed of the bearing components, and the geometry of the bearing and, therefore, the geometry of the lubricating film. In addition to the foregoing constraints, journal bearings must be configured to prevent excessive vibrations that may develop during rotation and cause contact between moving parts and possible damage to the bearing over time. Minute imbalances in the rotating member may initiate vibrations as the member rotates. Without adequate stability in the journal bearing system, vibrations may become excessive, resulting in oscillating motions of the bearing parts at relatively large amplitudes compared to the bearing clearances. Instability is usually mitigated, at least in part, by the selection of a suitable lubricant.

Not surprisingly, the fluid and lubricating characteristics of blood are unlike those of conventional lubricants such as oil. The use of blood as a lubricant in a blood pump journal bearing therefore presents unique problems. On one hand, it is crucial that the journal bearing maintain the integrity of the blood flowing through it and permit enough flow to adequately wash and cool the component parts of the pump. On the other hand, the journal dimensions must not be such that the dynamic stability of the bearing is compromised.

BRIEF SUMMARY OF THE INVENTION

The present invention contemplates a new and useful device that addresses the aforementioned problems and others by providing a blood pump incorporating a journal bearing geometry that ensures that the blood flow therethrough is adequate, that the integrity of the blood is preserved and that bearing stability is maintained. Briefly, the invention provides a lubricated journal bearing which is characterized by a non-circular geometry. The term "non-circular" as used herein refers to any cross-sectional geometry which is not a complete circle, i.e., a geometry that has a varying radius. "Non-circular" will encompass geometries that incorporate portions of constant radius. In one embodiment, the stationary bearing element, or stator, of the bearing is provided with a semi-elliptical shaped outer surface in an area opposite the load bearing film.

One advantage provided by the present invention is that a journal bearing constructed in accordance therewith provides an increase in the flow passage cross-sectional area and a corresponding increase in flow through the pump. This results in reduced residence times of blood within the pump and reduces the likelihood that thrombosis or protein accumulation will occur.

Another advantage provided by the present invention is that it provides an increase in the clearance between the rotor and stator elements in the blood pump, thereby reducing the shear stress in the blood flowing through the clearance and reducing the likelihood that hemolysis will occur.

Still another advantage provided by the present invention is that it provides a bearing journal that is characterized by an increase in stability and resistance to self-excited vibrations.

Other advantages and benefits of the present invention will become apparent to those skilled in the art upon a complete reading and understanding of the specification.

BRIEF DESCRIPTION OF THE DRAWINGS

The invention may take physical form in certain parts and arrangements of parts, preferred embodiments of which will be described in detail in this specification and illustrated in the accompanying drawings which form a part hereof and wherein.

DETAILED DESCRIPTION OF THE PREFERRED EMBODIMENTS

Figure 1:
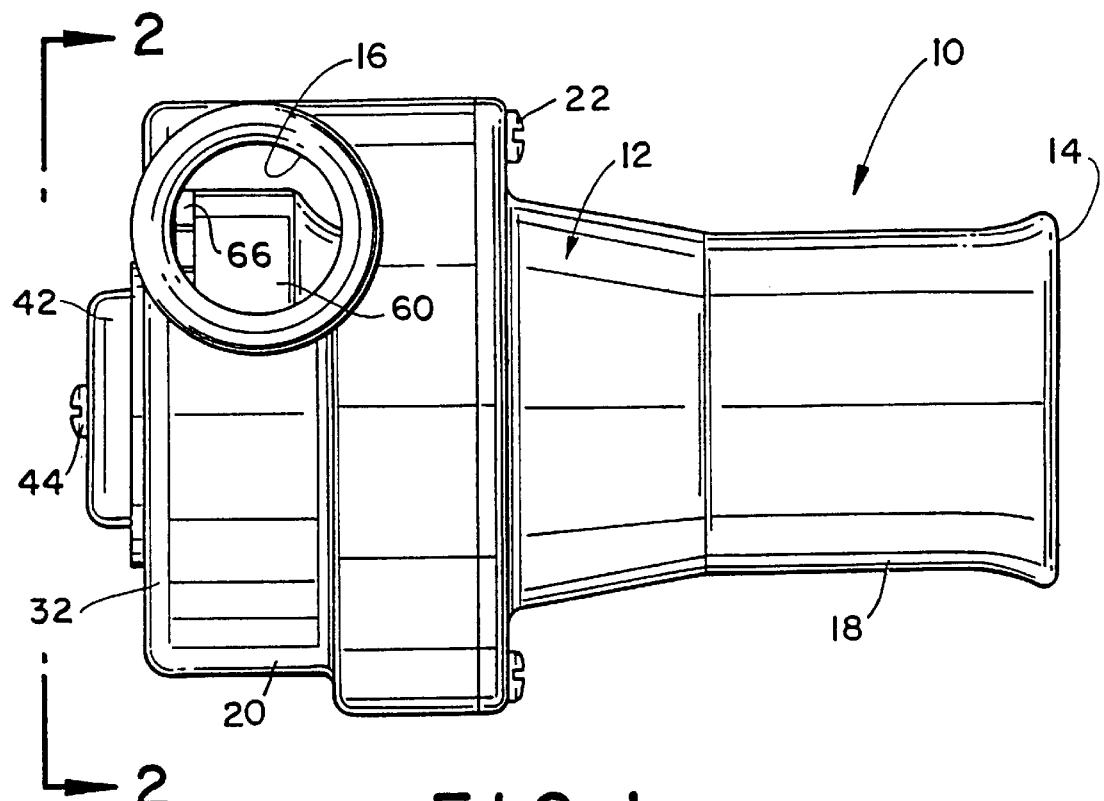
FIG. 1 is a side elevational view of a blood pump formed in accordance with the present invention and particularly showing the pump housing and inlet and outlet passageways.

Referring now to the drawings wherein the showings are for purposes of illustrating the preferred embodiments of the invention only and not for purposes of limiting same, the FIGURES show a pump 10 comprised of a housing 12, and having an inlet 14 and an outlet 16. While the drawings show an axial inlet, and a radial or tangential outlet, these are not essential features of the invention. In the blood application, the pump can be sized for implantation within a living body, and is preferably employed as an assist device for humans. It is to be noted that the pump can be sized so as to even be implantable within a heart chamber, avoiding the substantial problems of larger devices.

Figure 2:
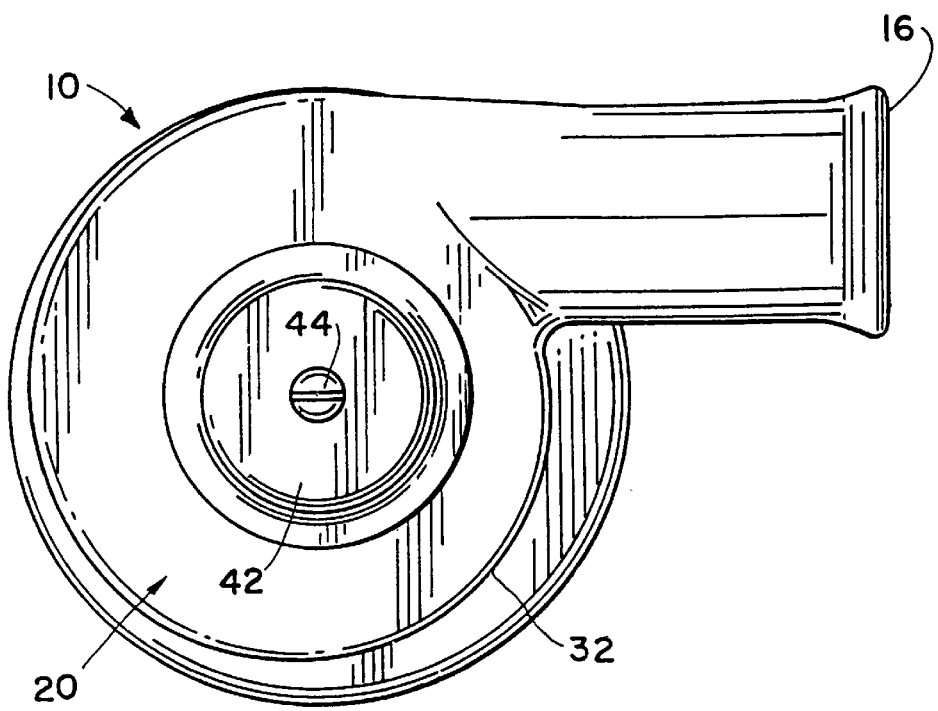
FIG. 2 is a left-hand end view taken generally along the lines 2—2 of FIG. 1.
Figure 3:
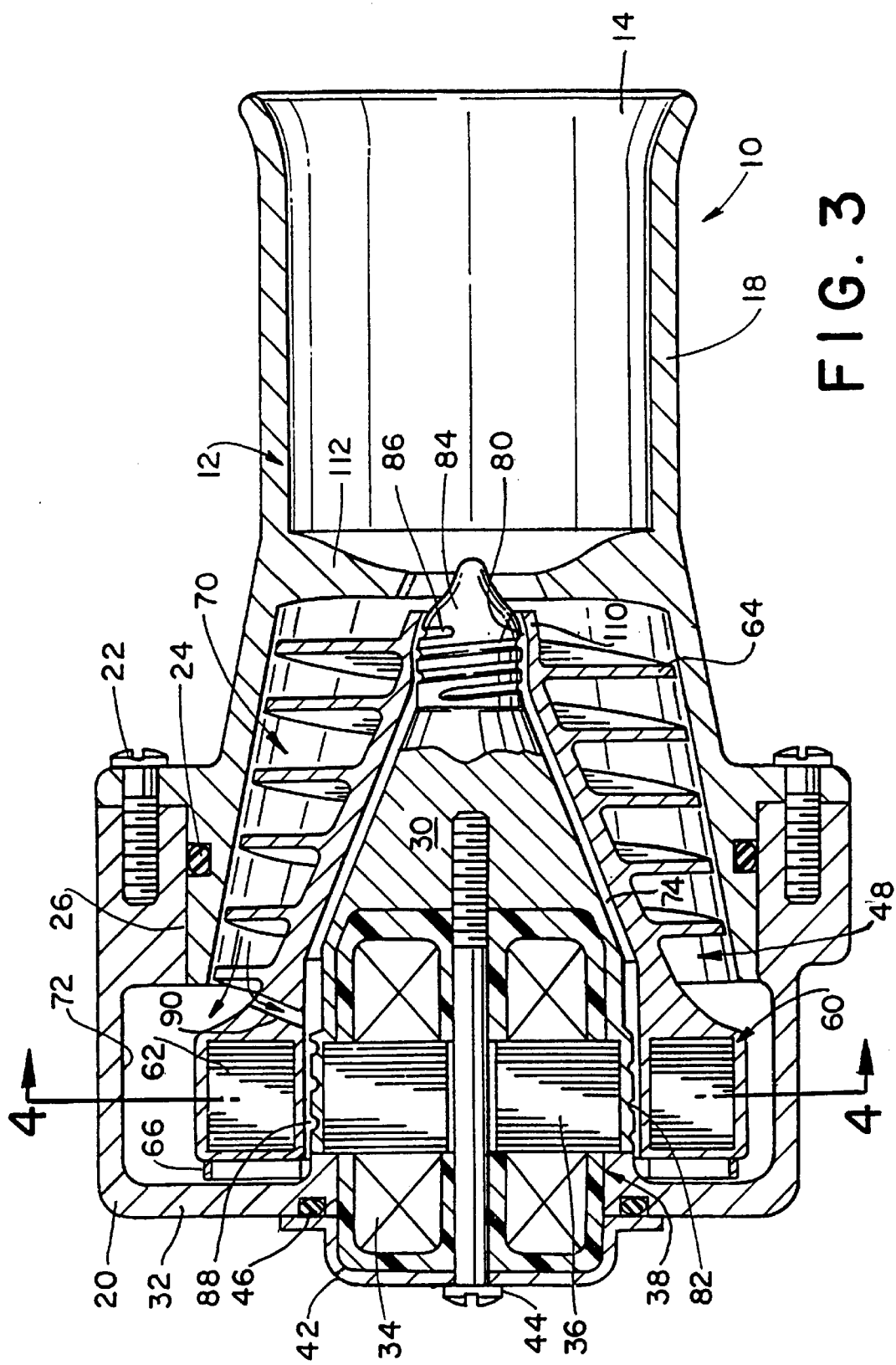
FIG. 3 is an enlarged, longitudinal cross-sectional view of a first preferred embodiment of the subject invention.

With particular relevance to FIGS. 1–3, the housing 12 is shown to be more particularly comprised of a rotor portion 18 and a drive housing or outlet portion 20, which in this particular embodiment partially houses the rotor as well as the drive means. Since in the preferred embodiments the pump is adapted for implantation in the living body, the housing portions are formed from a suitable, biocompatible material such as polished titanium. The housing portions 18, 20 are fastened together with conventional fastening devices 22 and sealed with a conventional sealing device such as an O-ring 24. The O-ring is positioned in an area of overlapping engagement 26 which has been made an interference fit or bonded so as to be gap free.

The housing portion 20 incorporates an axial extension 30 protruding from end wall 32. The axial extension receives motor windings 34 and lamination assembly or ferrous stack 36 of an electric motor 38. The motor is retained in the outlet housing portion by cover 42 and a fastener such as screw 44. The cover is sealed to the outlet housing portion with O-ring 46. The extension 30 protrudes a substantial dimension from the end wall, in fact, extending into the rotor housing portion and toward the inlet 14. This arrangement provides a generally annular pump chamber 48.

Received over the housing extension 30 is an annular rotor 60. The rotor includes an encapsulated permanent magnetic assembly 62, and first and second impeller blade sets 64, 66. There is no interconnecting shaft between the motor and impeller, i.e. a shaftless rotor. Further, a shaft seal between the motor and the impeller is eliminated, thus obviating many of the problems discussed above in prior art structures. In the preferred embodiment, the permanent magnet assembly 62 in the pump rotor 68 radially couples the rotor to the motor stator (stack and windings) through the non-magnetic wall of housing extension 30. It should be noted that this arrangement is essentially an inversion of the usual commercial motor arrangement, because the rotating element of the motor, i.e. the permanent magnetic assembly 62, is larger in diameter and encircles the stationary element, i.e. the stator 34, 36. This electric motor serves as the means for driving this embodiment of the invention insofar as it serves to create rotational motion of the pump rotor relative to the housing. The stator assembly is the drive element and the permanent magnet assembly the driven element of this version of a drive means.

With particular reference to FIG. 3, the first or primary impeller blade set 64 includes a plurality of mixed flow impeller blades. Radial flow or axial flow blade arrangements could also be encompassed within the scope of the invention. The impeller shown is a three-bladed variable lead screw. The secondary impeller blade set 66 is comprised of a plurality of radial flow impeller blades in this design embodiment.

The placement of rotor 60 in the housing 12 defines a continuous, first fluid passage 70 between the rotor 60 and the interior wall of the housing, which traverses from the inlet 14 to the annular output collector 72 of the pump chamber. A continuous second passage fluid passage 74 is formed between the housing extension 30 and the inside diameter of pump rotor 60. The second 74 has a generally large clearance, perhaps 0.020–0.030 inch, compared to the flow to be passed, but narrows to approximately 0.003–0.005 inch at opposite ends of the rotor to define first and second fluid bearings 80, 82 during operation of the pump. The first bearing 80 is located at the terminal end 84 of the portion of the motor housing extension 30 facing the inlet 14.

For improved pumping that avoids fluid damage or deposition due to sluggish or non-existing flow velocities through second passage 74, a continuous washing flow is required. The second set of impeller blades 66 scavenges blood from the second passage, discharging it to the collector 72. To prevent excessive pressure drop, a plurality of circumferentially spaced openings 90 extend generally radially between the first and second fluid passages to permit fluid to flow from the first to the second passage. Under the action of the pressure rise produced by the first blade set 64, flow traverses from openings 90 to impeller inlet 14, along passage 74. The second blade set also draws fluid from openings 90, through bearing 82, past end wall 32, and discharges the fluid into the collector 72.

Because the annular pump rotor 60 is freely received in the housing 12, it is important that its motion be controlled so that damage to the pumped fluid or the mechanical components does not result in close clearance areas, such as bearings 80, 82, or at interior walls of the housing. The symmetrical design of the pump permits the radial load to be low, which results in a significant fluid film thickness on the order of 0.001 inch at bearings 80, 82. This avoids mechanical wear on the pump components, and minimizes fluid shear of the blood, both of which are obviously detrimental to the intended use of the pump. On the other hand, if the load is too low, the bearings can get into a well-known whirl mode, destroying the film thickness and the bearings. In this operating mode, instead of rotating around a fixed axis, the rotor rolls 360 degrees around the stator, wearing all surfaces of the rotor and stator.

Figure 4:
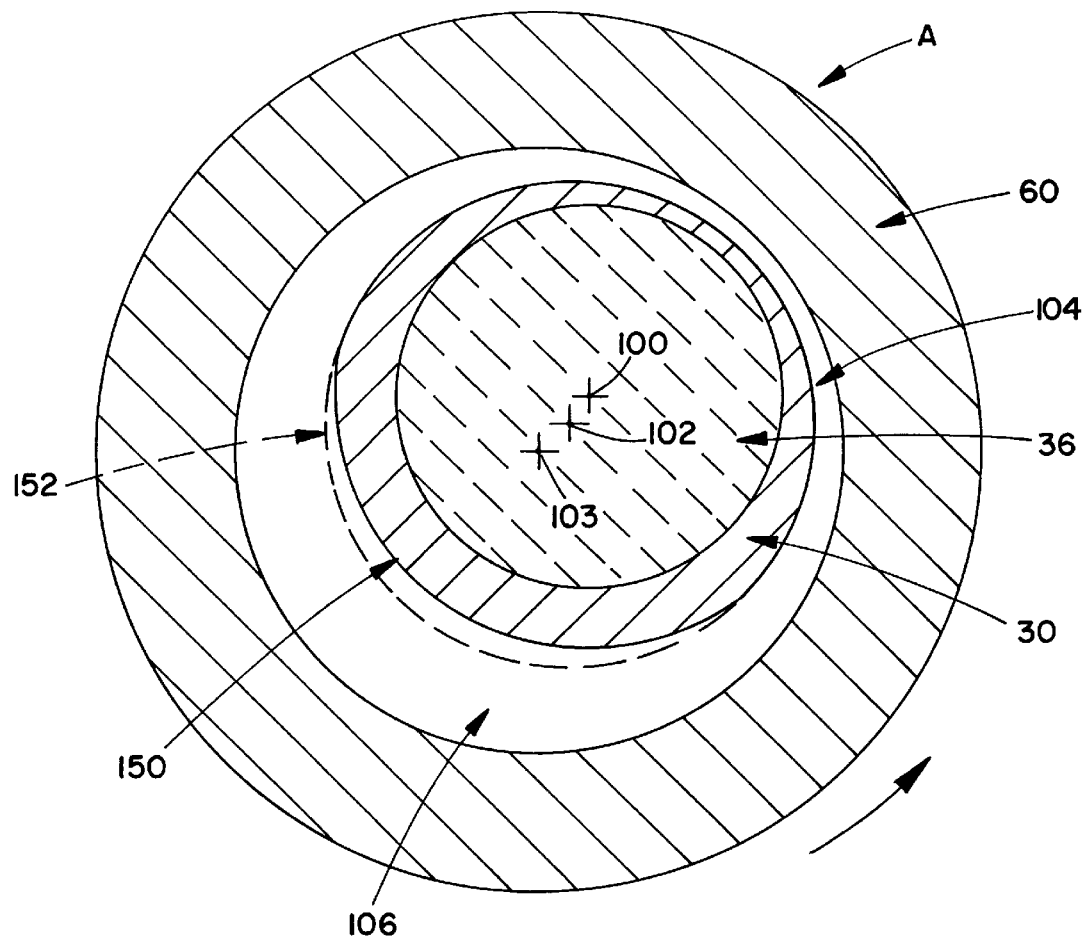
FIG. 4 is a schematic cross-sectional view taken along line 4—4 of FIG. 3 particularly illustrating the pump components and the non-circular geometry of the stationary bearing element.

FIG. 4 represents a cross-section taken along lines 4—4 in FIG. 3. Here rotor is represented generally by the annular region 60 and stator, or stationary bearing element, by the region 30. Region 36 represents the motor stator or driving element, which may be a ferrous stack of an electric motor or a motor winding assembly. In accordance with the invention described in U.S. Pat. No. 5,324,177, the centerline 100 of the driving element 36, is offset relative to the centerline 102 of the stationary bearing element or stator 30. As a result of this offset, magnetic forces are higher at region 104, and lower at region 106, resulting in a known, controlled magnitude and direction of bearing loading. The radial load on rotor will be the resultant force of gravity and the magnetic forces provided by the offset. The general direction of the radial load on 30 is represented by arrow A and the bearing load zone, generally in the region 104, provides a pressure distribution in the film of blood, which is entrained therein by viscous forces, to counter the radial load such that rotor 60 floats on stator 30.

In accordance with the present invention, the stator 30 is provided with a semi-elliptical surface 150 in an area opposite the load zone. Dotted line 152 represents a reference to a circular stator profile. As can be seen, the elliptical surface 150 provides an increase in the clearance between the rotor 60 and stator 30 in the general area 106. The elliptical surface has a major axis that corresponds to the diameter of the stator 30.

Figure 5:
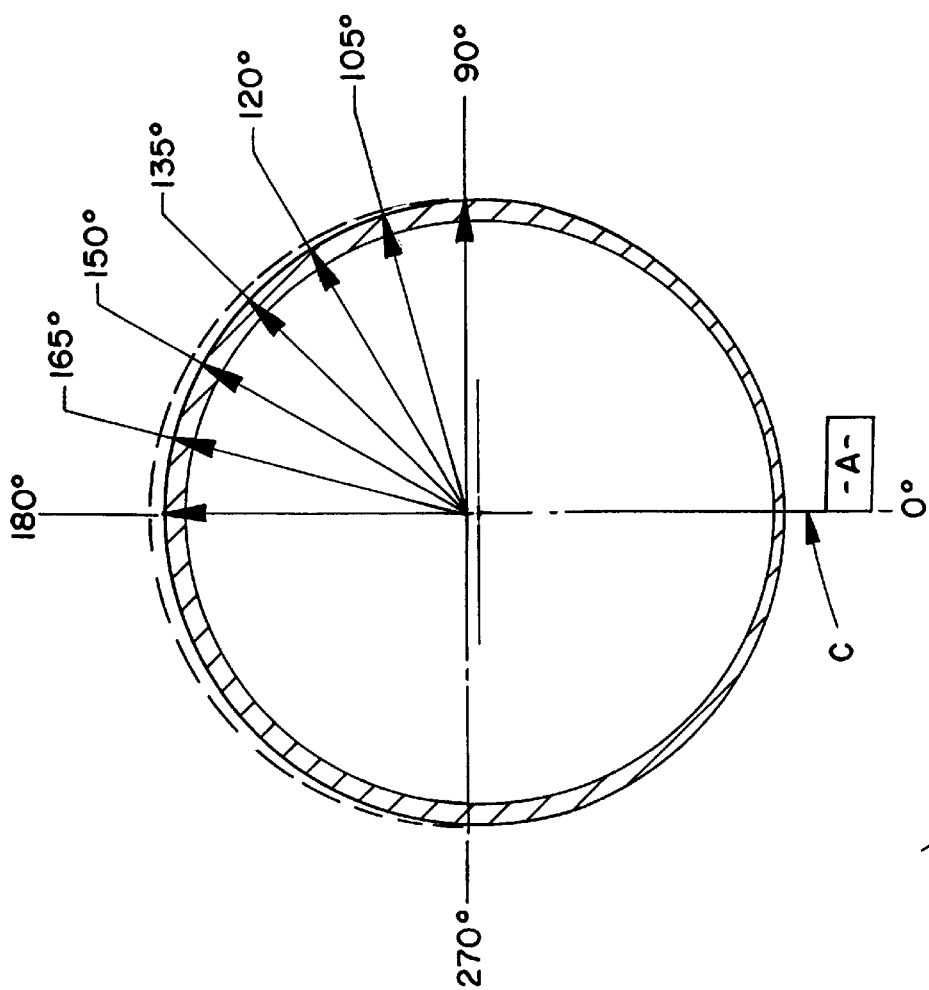
FIG. 5 is a cross-sectional view of a stator according to the present invention denoting the stator radius at various angles.

FIG. 5 illustrates in cross-section a preferred embodiment of a stator 30 according to the present invention. Table A denotes the stator radius at angles from 90 to 180 degrees from the load zone center C. It will be recognized that the same radius values apply to the angles from 180 to 270 degrees from the load zone center C in a symmetric fashion about the 180 degree point.

While the preferred embodiment of the invention is described with reference to a stator configuration comprising a half circle centered around the direction of offset of 100 and 102 (FIG. 4) mated with a semi-elliptical surface 150, it will be recognized that other dimensions and non-circular surface shapes are contemplated by the present invention. The foregoing description should therefore not be construed as limiting the invention. Rather, it is intended to illustrate the invention, the scope of which is defined in the appended claims.

What is claimed is:

1. A rotodynamic pump comprising:
    a housing having an axis, an inlet and outlet in fluid communication with a chamber,
    a rotor having an impeller received in the chamber; and
    a hydrodynamic bearing which includes a stationary bearing element for rotatably supporting the rotor, the stationary bearing element having, in radial cross-section, a non-circular geometry.

2. The pump defined in claim 1, wherein the non-circular geometry includes a circular portion.

3. The pump as defined in claim 1 wherein the geometry includes a semi-elliptical portion.

4. The pump as defined in claim 1 wherein the stationary bearing element extends within the rotor.

5. The pump as defined in claim 1 wherein the geometry includes a circular portion in a region near a load zone of the bearing and an elliptical portion in a region opposite the load zone.

6. The pump as defined in claim 1 further comprising a magnetic drive element for driving the rotor, the drive element being radially offset relative to an axis of the stationary bearing element to produce a predetermined radial force on the rotor.

7. The pump as defined in claim 1 wherein the stationary bearing element extends within the rotor and wherein the radial clearance between the rotor and the stationary bearing element is larger in an area opposite a load zone of the bearing than in the load zone.

8. A rotodynamic pump comprising:
    a housing having an axis and an inlet and an outlet in fluid communication with a chamber;
    a shaftless rotor received in the chamber for selective rotation relative to the housing;
    a drive for rotating the rotor relative to the housing including a drive element and a driven element operatively associated with the rotor; and
    a fluid bearing including a stationary bearing element for rotatably supporting the rotor, the stationary bearing element having, in radial cross-section, a non-circular geometry.

9. The pump defined in claim 8, wherein the non-circular geometry includes a circular portion.

10. The pump as defined in claim 8 wherein the geometry includes a semi-elliptical portion.

11. The pump as defined in claim 8 wherein the stationary bearing element extends within the rotor.

12. The pump as defined in claim 8 wherein the geometry includes a circular portion in a region near a load zone of the bearing and an elliptical portion in a region opposite the load zone.

13. The pump as defined in claim 8 further comprising a magnetic drive element for driving the rotor, the drive element being radially offset relative to an axis of the stationary bearing element to produce a predetermined radial force on the rotor.

14. The pump as defined in claim 8 wherein the stationary bearing element extends within the rotor and wherein the radial clearance between the rotor and the stationary bearing element is larger in an area opposite a load zone of the bearing than in the load zone.

15. A rotodynamic blood pump comprising:
    a housing having an inlet and an outlet in fluid communication with a chamber, the housing including a stationary bearing element that extends axially inward to the chamber from an end wall;
    an annular rotor received in the chamber around the stationary bearing element for selective rotation relative thereto, the rotor being spaced from the stationary bearing element and the housing to define radially spaced first and second passages, the first passage extending between the inlet and outlet and containing an impeller blade set on the rotor for urging flow from the inlet to the outlet;
    a drive for rotating the rotor relative to the housing, including a ferromagnetic assembly received in the rotor and an electric motor stator and winding assembly installed in the housing, an axis of the motor stator being radially displaced relative to an axis of the housing; and the second passage being narrowed to form a fluid bearing, the stationary bearing element having, in radial cross-section, a non-circular geometry.

16. The pump defined in claim 15, wherein the non-circular geometry includes a circular portion.

17. The pump as defined in claim 15 wherein the geometry includes a semi-elliptical portion.

18. The pump as defined in claim 15 wherein the stationary bearing element extends within the rotor.

19. The pump as defined in claim 15 wherein the geometry includes a circular portion in a region near a load zone of the bearing and an elliptical portion in a region opposite the load zone.

20. The pump as defined in claim 15 wherein the stationary bearing element extends within the rotor and wherein the radial clearance between the rotor and the stationary bearing element is larger in an area opposite a load zone of the bearing than in the load zone.

21. A rotodynamic pump comprising:

a housing having an axis, an inlet and outlet in fluid communication with a chamber;

a rotor having an impeller received in the chamber; and a stationary bearing element extending within the rotor for rotatably supporting the rotor, the stationary bearing element having, in radial cross-section, a non-circular geometry.

22. A rotodynamic pump comprising:

a housing having an axis, an inlet and outlet in fluid communication with a chamber;

a rotor having an impeller received in the chamber;

a stationary bearing element for rotatably supporting the rotor, the stationary bearing element having, in radial cross-section, a non-circular geometry; and a magnetic drive element for driving the rotor, the drive element being radially offset relative to an axis of the stationary bearing element to produce a predetermined radial force on the rotor.

* * * * *

(12) EX PARTE REEXAMINATION CERTIFICATE (5866th)
United States Patent
Golding et al.

(10) Number: US 5,890,883 C1
(45) Certificate Issued: Aug. 21, 2007

(54) ROTODYNAMIC PUMP WITH NON-CIRCULAR HYDRODYNAMIC BEARING JOURNAL

(75) Inventors: Leonard A. R. Golding, Moreland Hills, OH (US); William A. Smith, Lyndhurst, OH (US)

(73) Assignee: The Cleveland Clinic Foundation, Cleveland, OH (US)

Reexamination Request:
No. 90/007,558, May 25, 2005

Reexamination Certificate for:
Patent No.: 5,890,883
Issued: Apr. 6, 1999
Appl. No.: 08/820,756
Filed: Mar. 19, 1997

(51) Int. Cl.
*F04B 35/04* (2006.01)

(52) U.S. Cl. .................... 417/423.12; 604/151
(58) Field of Classification Search ............ 417/423.12, 417/423.1, 423.7, 423.13, 423.14; 604/151
See application file for complete search history.

(56) References Cited

U.S. PATENT DOCUMENTS

| | | |
|---|---|---|
| 3,201,183 A | 8/1965 | Buske |
| 3,218,981 A | 11/1965 | Kierulf |
| 3,420,184 A | 1/1969 | Englesberg et al. |
| 3,608,088 A | 9/1971 | Dorman et al. |
| 3,647,324 A | 3/1972 | Rafferty et al. |
| 3,846,050 A | 11/1974 | Laing |
| 3,960,468 A | 6/1976 | Boorse et al. |
| 4,135,253 A | 1/1979 | Reich et al. |
| 4,275,339 A | 6/1981 | Burke et al. |
| 4,382,199 A | 5/1983 | Isaacson |
| 4,438,542 A | 3/1984 | Schuh |
| 4,526,518 A | 7/1985 | Wiernicki |
| 4,625,712 A | 12/1986 | Wampler |
| 4,645,433 A | 2/1987 | Hauenstein |
| 4,688,998 A | 8/1987 | Olsen et al. |
| 4,704,121 A | 11/1987 | Moise |
| 4,779,614 A | 10/1988 | Moise |
| 4,806,080 A | 2/1989 | Mizobuchi et al. |
| 4,812,108 A | 3/1989 | Kotera |
| 4,927,407 A | 5/1990 | Dorman |
| 4,944,748 A | 7/1990 | Bramm et al. |
| 4,957,504 A | 9/1990 | Chardack |
| 5,030,018 A | 7/1991 | Korenblit |
| 5,036,235 A | 7/1991 | Kleckner |
| 5,044,897 A | 9/1991 | Dorman |
| 5,049,134 A | 9/1991 | Golding et al. |
| 5,055,005 A | 10/1991 | Kletschka |
| 5,112,202 A | 5/1992 | Oshima et al. |
| 5,158,440 A | 10/1992 | Cooper et al. |
| 5,169,242 A | 12/1992 | Blase et al. |
| 5,181,783 A | 1/1993 | Sherman et al. |
| 5,195,877 A | 3/1993 | Kletschka |
| 5,271,677 A | 12/1993 | Sherman et al. |
| 5,324,177 A | 6/1994 | Golding et al. |
| 5,370,509 A | 12/1994 | Golding et al. |
| 5,399,074 A | 3/1995 | Nose et al. |
| 5,695,471 A | 12/1997 | Wampler |
| 5,713,730 A | 2/1998 | Nose et al. |
| 5,840,070 A | 11/1998 | Wampler |
| 6,071,093 A | 6/2000 | Hart |
| 6,080,133 A | 6/2000 | Wampler |
| 6,116,862 A | 9/2000 | Rau et al. |

FOREIGN PATENT DOCUMENTS

| | | |
|---|---|---|
| DE | 41 23 433 A1 | 6/1992 |
| FR | A 2 102 520 | 7/1972 |
| GB | 871001 | 6/1961 |
| WO | WO 91/19103 | 12/1991 |
| WO | WO 94 09274 A | 4/1994 |

*Primary Examiner*—Matthew C. Graham

(57) ABSTRACT

A blood pump incorporates a blood lubricated journal bearing that is characterized by a non-circular geometry. In one embodiment, the stationary bearing element, or stator, of the bearing is provided with a semi-elliptical shaped outer surface in an area opposite the load bearing film. The journal bearing configuration ensures that the blood flow therethrough is adequate, that the integrity of the blood is preserved and that bearing stability is maintained.

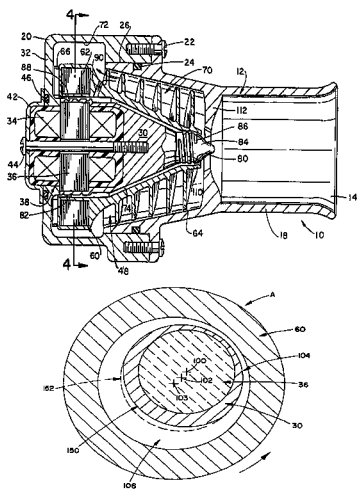

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentablilty of claims 1–22 is confirmed.

\* \* \* \* \*